(12) United States Patent
Bi et al.

(10) Patent No.: US 7,962,428 B2
(45) Date of Patent: Jun. 14, 2011

(54) SYSTEM AND METHOD FOR JOINT OPTIMIZATION OF CASCADED CLASSIFIERS FOR COMPUTER AIDED DETECTION

(75) Inventors: Jinbo Bi, Chester Springs, PA (US); Murat Dundar, Malvern, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 752 days.

(21) Appl. No.: 11/947,111

(22) Filed: Nov. 29, 2007

(65) Prior Publication Data

US 2008/0147577 A1   Jun. 19, 2008

Related U.S. Application Data

(60) Provisional application No. 60/867,970, filed on Nov. 30, 2006.

(51) Int. Cl.
*G06E 1/00* (2006.01)
(52) U.S. Cl. ............................ 706/20; 382/118; 382/103
(58) Field of Classification Search .................. 706/20; 382/103, 118
See application file for complete search history.

(56) References Cited

U.S. PATENT DOCUMENTS

| | | | | |
|---|---|---|---|---|
| 2003/0200188 | A1* | 10/2003 | Moghaddam | 706/25 |
| 2005/0180627 | A1* | 8/2005 | Yang et al. | 382/159 |
| 2006/0112038 | A1* | 5/2006 | Luo | 706/20 |
| 2006/0257017 | A1* | 11/2006 | Luo | 382/159 |
| 2007/0076959 | A1* | 4/2007 | Bressan | 382/224 |

OTHER PUBLICATIONS

"Rapid Object Detection Using a Boosted Cascade of Simple Features", Paul Viola, Michael Jones, Computer Vision and Pattern Recognition, 2001, CVPR 2001, Proceedings of the 2001 IEEE Computer Society Conference on, vol. 1, 2001, pp. I-511-I-518.*
"Inter-stage Feature Propagation in Cascade Building with Adaboost", Jan Sochman, Jiri Matas, Pattern Recognition, 2004, ICPR 2004, Proceedings of the 17th International Conference on, vol. 1, 2004, pp. 236-239.*
"Robust object detection via soft cascade", Lubomir Bourdev, Jonathan Brandt, Computer Vision and Pattern Recognition, 2005, CVPR 2005, IEEE Computer Society Conference on, vol. 2, 2005, pp. 236-243.*
Bi et al., "Computer Aided Detection Via Asymmetric Cascade of Sparse Hyperplane Classifiers", KDD '06, Aug. 20-23, 2006, Philadelphia, PA, USA, 8 pages.

* cited by examiner

*Primary Examiner* — David R Vincent
*Assistant Examiner* — Mai T Tran
(74) *Attorney, Agent, or Firm* — Peter Withstandley

(57) ABSTRACT

A method for training classifiers for Computer-Aided Detection in medical images includes providing an image feature training set $\{(x_i, y_i)\}_{i=1}^{l}$, wherein $x_i \in R^d$ are input feature variables and $y_i \in \{-1,1\}$ are class labels, and a cascade of K classifiers to be trained, minimizing, for each classifier k, a first cost function to initialize an $\alpha_k^0$ associated with each classifier k, fixing all classifiers except classifier k and minimizing a second cost function to solve for $\alpha_k^c$ for a counter value c using the training dataset $\{(x_i^k, y_i)\}_{i=1}^{l}$, calculating a third cost function $J^c(\alpha_1^c, \ldots, \alpha_K^c)$ for each classifier k, and comparing $J^c$ with a previous iteration $J^{c-1}$, wherein if $J^c - J^{c-1}$ is less than a predetermined tolerance, said classifier training is completed.

20 Claims, 4 Drawing Sheets

|  | AND-OR Cascade | | | SVM | Cascade AdaBoost | | | | |
|---|---|---|---|---|---|---|---|---|---|
|  | | | | | Phase 1 | Phase 2 | Phase 3 | | |
|  | $C_1$ | $C_2$ | $C_3$ | | $C_1$ | $C_2$ | $C_3$ | $C_4$ | $C_5$ |
| Avg. CPU time per volume (sec.) | 28 | 27.5 | 25.48 | 294.0 | 26.0 | 25.0 | 67.48 | | |
| number of polyps found (out of 106) | 105 | 100 | 100 | 99 | 103 | 103 | 102 | 102 | 91 |
| False positives per volume (initially 139.4) | 55 | 18.2 | 5 | 5 | 50 | 48.2 | 30.8 | 20.6 | 5.0 |

SYSTEM AND METHOD FOR JOINT OPTIMIZATION OF CASCADED CLASSIFIERS FOR COMPUTER AIDED DETECTION

CROSS REFERENCE TO RELATED UNITED STATES APPLICATIONS

This application claims priority from "Collaborative Learning of Cascaded Classifiers for Computer Aided Diagnosis", U.S. Provisional Application No. 60/867,970 of Bi, et al., filed Nov. 30, 2006, the contents of which are herein incorporated by reference.

TECHNICAL FIELD

This disclosure is directed to Computer Aided Detection methods for classifying and identifying structures of interest in medical images.

DISCUSSION OF THE RELATED ART

Over the past decade, Computer-Aided Detection (CAD) systems have moved from the realm of academic publications to robust commercial systems that are used by physicians in their clinical proactive to help detect early cancer from medical images. The growth has been fueled by a Food and Drug Administration (FDA) decision to grant approval in 1998 for a CAD system that detected breast cancer lesions from mammograms. Since then a number of CAD systems have received FDA approval. Virtually all of these commercial CAD systems focus on detection of breast cancer lesions for mammography. The CAD concept can be generalized to many other detection tasks in medical image analysis, such as lung nodule detection and colon polyp detection.

A CAD system is usually used by physicians as a second reader in their clinical practice in the middle of their diagnostic analysis to help detect early cancer from medical images. There is a real-time requirement that a CAD system needs to satisfy. On the other hand, high sensitivity is also useful for a CAD system. This involves identification of a large set of candidates in an image because any cancer that is missed at this stage can never be found by the CAD system. For every candidate identified, a large number of features are computed to describe the target structure. Thus, high sensitivity and run-time performance are two conflicting goals for a CAD system.

Many CAD systems make use of cascaded classifiers for real-time object detection. A typical workflow for object detection in a new patient image is as follows.

1. Identify candidate structures in the image: In 2D object detection this is achieved by taking sub-windows of the image at different scales. Each sub-window is a candidate. In 3D lesion detection from medical images, particularly image volumes generated by high-resolution computed tomography (CT), a more sophisticated candidate generation algorithm based on the image/shape characteristics of the lesion is required. Typically, and efficient image processing algorithm considers each pixel or voxel in the image as a potential candidate seed, and selects a fraction of seeds as candidates.

2. Extract features for each candidate: A number of image features are usually calculated to describe the target structure.

3. Classify candidates as positive or negative: A previously-trained classifier is used to label each candidate.

4. Display positive candidates: Typically, the digitized image is displayed with marks for inspection by the physician.

In the candidate identification stage, even a small fraction of the seeds is necessarily very large to maintain high sensitivity. High sensitivity (ideally close to 100%) is useful, because any target structure missed at this stage can never be found by the system, which otherwise may be detected later in the classification stage by exploring effective features. Hence, many false positives are generated at this stage (less than 1% of the candidates are positive), which makes the classification highly unbalanced. Moreover, CAD systems need to be fast enough for physicians to use in their diagnostic analysis.

FIG. 1 depicts an exemplary cascade classification scheme comprising a sequence of classifiers 1, 2, . . . K of increasing complexity. The input at each stage k is a set of candidates $T_{k-1}$, where each stage rejects a subset of candidates $F_k$ as being negative. Reducing computation time and speeding-up online learning can be achieved by designing simpler yet highly sensitive classifiers in the earlier stages of the cascade to reject as many negative candidates as possible before calling upon classifiers with more complex features to further reduce the false positive rate. A positive result from the first classifier activates the second classifier and a positive result from the second classifier activates the third classifier, and so on. A negative outcome for a candidate at any stage in the cascade leads to an immediate rejection of that candidate. Under this scenario $T_{k-1} = T_k \cup F_k$ and $$T_0 = T_K \cup \bigcup_i^K F_k$$

where $T_k$ and $F_k$ are the sets of candidates labeled as positive and negative respectively by classifier k.

Previous cascade classification approaches are mostly based on AdaBoost. Cascade AdaBoost is a useful tool for building real-time robust applications, especially for object detection systems. However, cascade AdaBoost works with two implicit assumptions: (1) a significant amount of representative data is available for training the cascade classifier; and (2) all features can be equally evaluated with a relatively low computational cost. These assumptions, unfortunately, often do not hold for CAD systems. Available data can be noisy and hardly represents all aspects of the target characteristics. One concern about cascade classification approaches is that if a classifier within the cascade does not generalize well and hence screens out more true positives than necessary, then these true positives will never be recovered at later stages. The more stages in the cascade, the riskier the system becomes. This observation suggests a cascade design having significantly fewer stages. Furthermore, simple and low-cost image features are often not sufficient for detecting target structures, especially in 3D medical images. Advanced features are useful for performance enhancement, but require more computation time. If these features need to be calculated for a large portion of the candidates at the early stage of the cascade, the system may become prohibitively slow. Cascade AdaBoost treats all features equally when selecting features for each individual stage classifier, which leads to a computational inefficiency.

Another cascade approach for Computer Aided Detection (CAD), disclosed in co-pending application of Bi, et al., "System and Method for Computer Aided Detection via Asymmetric Cascade of Sparse Linear Classifiers", U.S. patent application Ser. No. 11/592,869, filed Nov. 3, 2006, the contents of which are herein incorporated by reference in their entirety, incorporates the computational complexity of features into the cascade design. The cascading strategy in this approach has the following features. (1) High computational efficiency: early stages weed out many non-target patterns, so most stages are not evaluated for a typical negative candidate. Computationally expensive features are only calculated for a small portion of the candidates at later stages. (2) Robust system: a linear program with an $l_1$-norm regularization is incorporated at each stage. A cascade of very few stages is unlikely to harm the robustness of the linear classifiers, opposed to a cascade of over 20 stages that often occurs using AdaBoost.

The issue with the cascade AdaBoost and other greedy cascade classifiers including the above approach is that each classifier serves its own purpose by optimizing a local problem without worrying about the overall performance. The cascade is trained by sequentially optimizing the classifiers at each stage. This training scheme potentially limits the performance of the overall system. For example, there may be positive candidates in the dataset which would be correctly classified at stage K. These candidates could be compromised for a bulk of negative candidates earlier in the cascade to gain significant computational advantages without sacrificing the overall sensitivity. Likewise some positives which are missed in the earlier stages could have otherwise be detected in later stages with the help of additional features. Since the cascade is trained sequentially using the framework in FIG. 1, cascade AdaBoost and other greedy cascade classifiers do not fully exploit the potential of a cascaded framework.

SUMMARY OF THE INVENTION

Exemplary embodiments of the invention as described herein generally include computer-implemented methods and systems for cascade classification schemes using an AND-OR framework for learning the classifiers in the cascade. The classifiers in the cascade are jointly trained to achieve optimization at the system level, i.e. maximize the area of the region of interest under a Receiver Operating Characteristics (ROC) curve at stage K. An example is classified as positive by the cascade if it is labeled as positive by all the stages and it is classified as negative if it is rejected at any stage in the cascade. An offline training scheme is based on the joint optimization of the classifiers in the cascade to minimize an overall objective function. The design parameters for an individual classifier may be updated depending on how well the other classifiers are performing. Since a framework according to an embodiment of the invention is optimized at the system level, some of the classifiers in the cascade may yield suboptimal performances.

An implementation of a classification formulation through alternating optimization techniques is described. Preliminary convergence analysis shows that an algorithm according to an embodiment of the invention converges to a cascade of classifiers where each classifier in the cascade is a fixed point of the algorithmic mapping, and hence optimal when the cascade is fixed in any other stages. An algorithm according to an embodiment of the invention focuses on offline training of the classifiers and does not necessarily restrict how the classifiers should be ordered in the cascade sequence. The order of the classifiers is problem-specific in the cascade design. Any suitable domain or prior knowledge can be used to determine it. Experiments indicate that the computational complexity of different sets of features is a factor in deciding which classifiers need to be executed earlier, and which later.

A classification approach according to an embodiment of the invention is applied to automatically detect polyps from multi-slice CT images. Execution speed of the CAD system is improved while yielding comparable performance with the current state-of-the-art, and yields favorable results over Cascade AdaBoost both in terms of performance and online execution speed.

According to an aspect of the invention, there is provided a computer-implemented method for training classifiers for Computer-Aided Detection in medical images, the method performed by the computer including providing an image feature training set $\{(x_i, y_i)\}_{i=1}^l$, wherein $x_i \in R^d$ are input feature variables and $y_i \in \{-1,1\}$ are class labels for labeling each variable and a cascade of K classifiers to be trained, minimizing, for each classifier k, a first cost function $$\Phi(\alpha_k) + \sum_{i=1}^{l} w_i \times \max(0, 1 - \alpha^T y_i x_i^k)$$

to initialize an $\alpha_k^0$ associated with each classifier k, wherein the function $\Phi:R^{(d)} \Rightarrow R$ is a regularization function and $\{w_i : w_i \geq 0, \forall i\}$ is a pre-determined weight associated with $x_i$, for each classifier k, fixing all classifiers except classifier k and minimizing a second cost function $\Phi_k(\alpha_k) + v_1 \Sigma_{i \in C^-} w_i \times \max(0, e_{ik}) + v_2 \Sigma_{i \in C^+} \max(0, e_{i1}, \ldots, e_{ik}, \ldots, e_{iK})$ to solve for $\alpha_k^c$ for a counter value c using the training dataset $\{(x_i^k, y_i)\}_{i=1}^l$, wherein $$w_i = \prod_{m=1, m \neq k}^{K} \max(0, e_{im}),$$

$e_{ik} = 1 - \alpha_k^T y_i x'_{ik}$ defines a hinge loss of the $i^{th}$ training example $\{(X'_{ik}, y_i)\}$ induced by classifier k, $v_1$ and $v_2$ are weighting factors, $C^{30}$ and $C^-$ are corresponding sets of indices for positive and negative classes respectively, and wherein $x'_{ik}$ denotes the subset of features in $x_i$ used by classifier k, calculating $$J^c(\alpha_1^c, \ldots, \alpha_K^c) = \sum_{k=1}^{K} \Phi_k(\alpha_k^c) + v_1 \sum_{i \in C^-} \prod_{k=1}^{K} \max(0, e_{ik}) + v_2 \sum_{i \in C^+} \max(0, e_{i1}, \ldots, e_{iK})$$

for each classifier k and comparing $j^c$ with a previous iteration $j^{c-1}$, wherein if $J^c - j^{c-1}$ is less than a predetermined tolerance, said classifier training is completed.

According to a further aspect of the invention, providing an image feature training set comprises providing a set of image features, said features generated from one or more digitized medical images, each said image comprising a plurality of intensities associated with an n-dimensional grid of points, partitioning said image feature set into a plurality of subsets according to a computational cost of classifying a candidate feature as one of said image features, developing a feature classifier wherein each image feature subset is associated with a feature classifier, and forming of cascade of said classifiers of increasing complexity.

According to a further aspect of the invention, the first cost function is solved as a mathematical programming system $$\min_{(\alpha,\xi)\in R^{d+1}} \Phi(\alpha) + \sum_{i=1}^{l} w_i \xi_i$$

such that $$\xi_i \geq 1 - \alpha^T y_i x_i,$$

$$\xi_i \geq 0, \forall i.$$

According to a further aspect of the invention, the second cost function is solved as a mathematical programming system $$\min_{(\alpha_k,\xi_k)\in R^{d_k+1}} \Phi_k(\alpha_k) + v_1 \sum_{i\in C^-} w_i \xi_i + v_2 \sum_{i\in C^+} \xi_i,$$

such that $$\xi_i \geq e_{ik}, \forall i,$$

$$\xi_i \geq 0, \forall i \in C^-,$$

$$\xi_i \geq \gamma_i, \forall i \in C^+,$$

wherein $y_i = \max(0, e_{i1}, \ldots, e_{i(m-1)}, e_{i(m+1)}, \ldots, e_{iK})$.

According to a further aspect of the invention, the method includes tuning values of said weighting factors $v_1$ and $v_2$ to maximize an area under a receiver operator characteristic (ROC) curve corresponding to a domain of 0 to 5 false positives per image.

According to a further aspect of the invention, the trained classifiers are adapted to being used in a cascade of classifiers of increasing complexity that detect and classify regions of interest in incoming medical images.

According to a further aspect of the invention, $\Phi(\alpha) = \|\alpha\|_2^2$.

According to a further aspect of the invention, $\Phi(\alpha) = |\alpha|$.

According to a further aspect of the invention, the method includes incrementing a counter c, and terminating said training if said counter becomes greater than a pre-determined maximum.

According to another aspect of the invention, there is provided a program storage device readable by a computer, tangibly embodying a program of instructions executable by the computer to perform the method steps for training classifiers for Computer-Aided Detection in medical images.

According to another aspect of the invention, there is provided computer-implemented method for training classifiers for Computer-Aided Detection in medical images, the method performed by the computer including providing an image feature training set $\{(x_i, y_i)\}_{i=1}^{l}$, wherein $x_i \in R^d$ are input feature variables and $y_i \in \{-1,1\}$ are class labels for labeling each variable and a cascade of K hyperplane classifiers to be trained, training said cascade of hyperplane classifiers using said training set wherein a negative candidate is correctly classified by said cascade when it is rejected by at least one of said classifiers, and a positive candidate is correctly classified if it is detected by all of the classifiers in the cascade.

According to a further aspect of the invention, the method includes providing an initial set $\alpha_k^0$ associated with each classifier k by minimizing, for each classifier k, a first cost function $$\Phi(\alpha_k) + \sum_{i=1}^{l} w_i \times \max(0, 1 - \alpha^T y_i x_i^k),$$

wherein the function $\Phi: R^{(d)} \Rightarrow R$ is a regularization function and $\{w_i: w_i \geq 0, \forall i\}$ is a pre-determined weight associated with $x_i$, and, at each iteration of the classifier training, given a set $\alpha_k^c$ from a previous iteration, solving for $\alpha_k^{c+1}$ for each classifier k by fixing all classifiers except classifier k and minimizing a second cost function $\Phi_k(\alpha_k) + v_1 \sum_{i\in C^-} w_i \times \max(0, e_{ik}) + v_2 \sum_{i\in C^+} \max(0, e_{i1}, \ldots, e_{ik}, \ldots, e_{iK})$ using the training dataset $\{(x_i^k, y_i)\}_{i=1}^{l}$, wherein $$w_i = \prod_{m=1, m\neq k}^{K} \max(0, e_{im}),$$

$e_{ik} = 1 - \alpha_k^T y_i x_{ik}'$ defines a hinge loss of the $i^{th}$ training example $\{(x_{ik}', y_i)\}$ induced by classifier k, $v_1$ and $v_2$ are weighting factors, $C^+$ and $C^-$ are corresponding sets of indices for positive and negative classes respectively, and $x_{ik}'$ denotes the subset of features in $x_i$ used by classifier k.

According to a further aspect of the invention, the method includes calculating a third cost function $$J^{c+}(\alpha_1^{c+1}, \ldots, \alpha_K^{c+1}) =$$

$$\sum_{k=1}^{K} \Phi_k(\alpha_k^{c+1}) + v_1 \sum_{i\in C^-} \prod_{k=1}^{K} \max(0, e_{ik}) + v_2 \sum_{i\in C^+} \max(0, e_{i1}, \ldots, e_{iK})$$

from the set of $\alpha_k^{c+1}$ for each classifier k, and comparing $J^{c+1}$ with a previous iteration $J^c$ to determine if said training is complete.

DETAILED DESCRIPTION OF EXEMPLARY EMBODIMENTS

Figure 1:
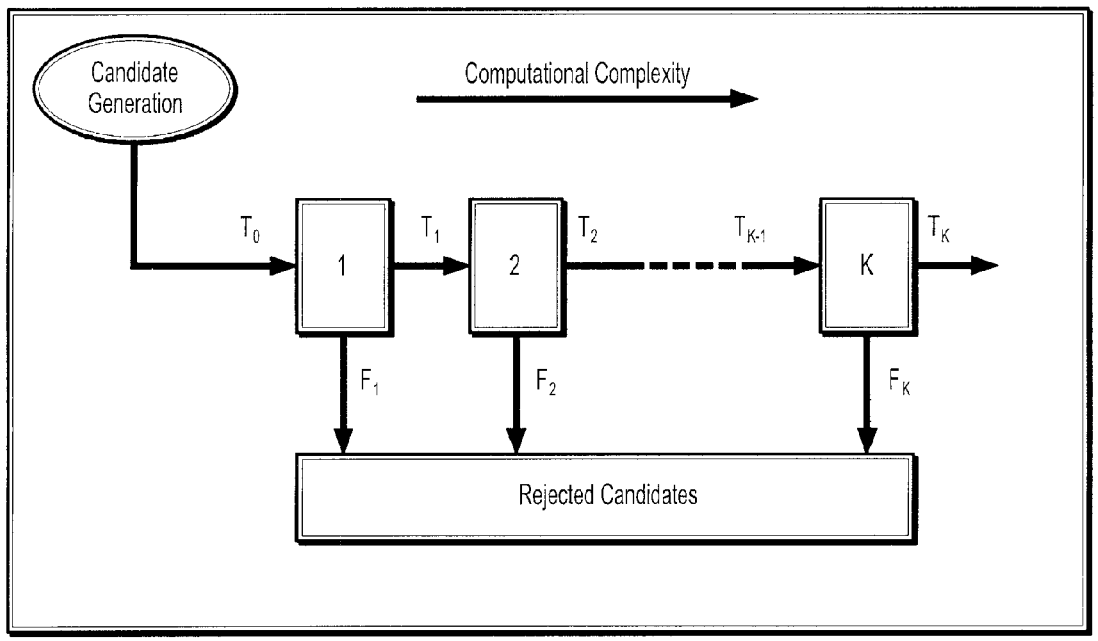
FIG. 1 depicts a typical cascade classification scheme for online classification and offline training.

Exemplary embodiments of the invention as described herein generally include systems and methods for classifying and identifying structures of interest in medical images. Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

As used herein, the term "image" refers to multi-dimensional data composed of discrete image elements (e.g., pixels for 2-D images and voxels for 3-D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to $R$, the methods of the inventions are not limited to such images, and can be applied to images of any dimension, e.g., a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

Collaborative Cascaded Learning (CCL)

A feature vector $x_i \in R^d$ is assumed to be partitioned in to K subsets of non-overlapping variables in the order of increasing computational complexity as $x_i = (\bar{x}_{i1}, \ldots, \bar{x}_{iK})$, with $\bar{x}_{ik} \in R^{p_k}$ for $k=1, \ldots K$, $$\sum_{k=1}^{K} p_k = d.$$

The feature set at stage k is the accumulative set of all the k features subsets, i.e. $x_{ik}' = [\bar{x}_{i1}, \ldots, \bar{x}_{ik}]$ and $x_{iK}' = x_i$.

The cascade is constructed by sequentially training the classifiers. The training set at stage k is $\{(x_i', y_i)\}$, for $i \in \Psi_{k-1}$, where $\Psi_{k-1}$ is the set of indices of candidates classified positive by the classifier at stage k-1, $\Psi_{k-1} = \{i: x_i \in T_{k-1}\}$. In this framework each classifier eliminates as many negative candidates as possible while satisfying the designated sensitivity and leaving the remaining candidates to the next classifier in line. Even though the data becomes more balanced by weeding out many non-target structures in the earlier stages, the classification task becomes more and more challenging when the data reaches later stages. The newly added features at each stage may provide extra flexibility for the classifier, but there is no guarantee these features will help remove the remaining false positives.

Hyperplane Classifiers

Before describing the AND-OR framework, hyperplane classifiers will be reviewed. Consider a training dataset $\{(x_i, y_i)\}_{i=1}^{l}$ where $x_i \in R^d$ are input variables and $y_i \in \{-1, 1\}$ are class labels. One considers a class of models of the form $f(x) = \alpha^T x$, with the sign of $f(x)$ predicting the label associated with the point x. A hyperplane classifier with hinge loss can be designed by minimizing the following cost function:

$$J(\alpha) = \Phi(\alpha) + \sum_{i=1}^{l} w_i (1 - \alpha^T y_i x_i)_+ \quad (1)$$

where the function $\Phi: R^{(d)} \Rightarrow R$ is a regularization function or regularizer on the hyperplane coefficients and $(k)_+ = \max(0, k)$ represents the hinge loss, and $\{w_i: w_i \geq 0, \forall i\}$ is the weight pre-assigned to the loss associated with $x_i$. For balanced data usually $w_i = w$, but for unbalanced data it is a common practice to weight positive and negative classes differently, i.e. $\{w_i = w_+, \forall i \in C^+\}$ and $\{w_i = w_-, \forall i \in C^-\}$ where $C^+$ and $C^-$ are the corresponding sets of indices for the positive and negative classes respectively.

The function $(1 - \alpha^T y_i x_i)_+$ is a strictly convex function. The weighted sum of strictly convex functions is also strictly convex. Therefore for a strictly convex function $\Phi(\alpha)$ is also strictly convex. The system in EQ. (1) can be formulated as a mathematical programming system as follows:

$$\min_{(\alpha, \xi) \in R^{d+1}} \Phi(\alpha) + \sum_{i=1}^{l} w_i \xi_i \quad (2)$$

$$\text{such that } \begin{array}{l} \xi_i \geq 1 - \alpha^T y_i x_i, \\ \xi_i \geq 0, \forall i. \end{array}$$

For $\Phi(\alpha) = \|\alpha\|_2^2$, EQ. (2) results in a conventional Quadratic-Programming-SVM (Support Vector Machine), and for $\Phi(\alpha) = |\alpha|$, it yields a sparse Linear-Programming-SVM.

AND-OR Learning Framework

As discussed earlier, previous cascaded classification approaches train classifiers sequentially for each different stage, which amounts to a greedy scheme, meaning that the individual classifier is optimal only to the corresponding specific stage. The classifiers are not necessarily optimal to the overall structure where all stages are taken into account. A cascaded classifier training approach according to an embodiment of the invention optimizes all of the classifiers in the cascade in parallel by minimizing the regularized risk of the entire system and providing implicit mutual feedback to individual classifiers to adjust parameter design.

More specifically, assume the feature vector $x_i \in R^d$ is partitioned into K subsets of non-overlapping variables in the order of increasing computational complexity as $x_i = (\bar{x}_{i1}, \ldots, \bar{x}_{iK})$, with $\bar{x}_{ik} \in R^{p_k}$ for $k=1, \ldots, K$, $$\sum_{k=1}^{K} p_k = d.$$

The feature set at stage k is the accumulative set of all the k feature subsets i.e. $x_{ik}' = [\bar{x}_{i1}, \ldots, \bar{x}_{ik}]$ and $x_{iK}' = x_i$.

In the greedy scheme, shown in FIG. 1, the training set at stage k is $\{(x_i', y_i)\}$, for $i \in \Psi_{k-1}$, where $\Psi_{k-1}$ is the set of indices of candidates classified positive by classifier at stage k-1, $\Psi_{k-1} = \{i: x_i \in T_{k-1}\}$. In this framework each classifier eliminates as many negative candidates as possible while satisfying the designated sensitivity and leaving the remaining candidates to the next classifier in line, thus $\Psi_K \subset \Psi_{K-1} \subset \ldots \subset \Psi_0$.

Figure 2:
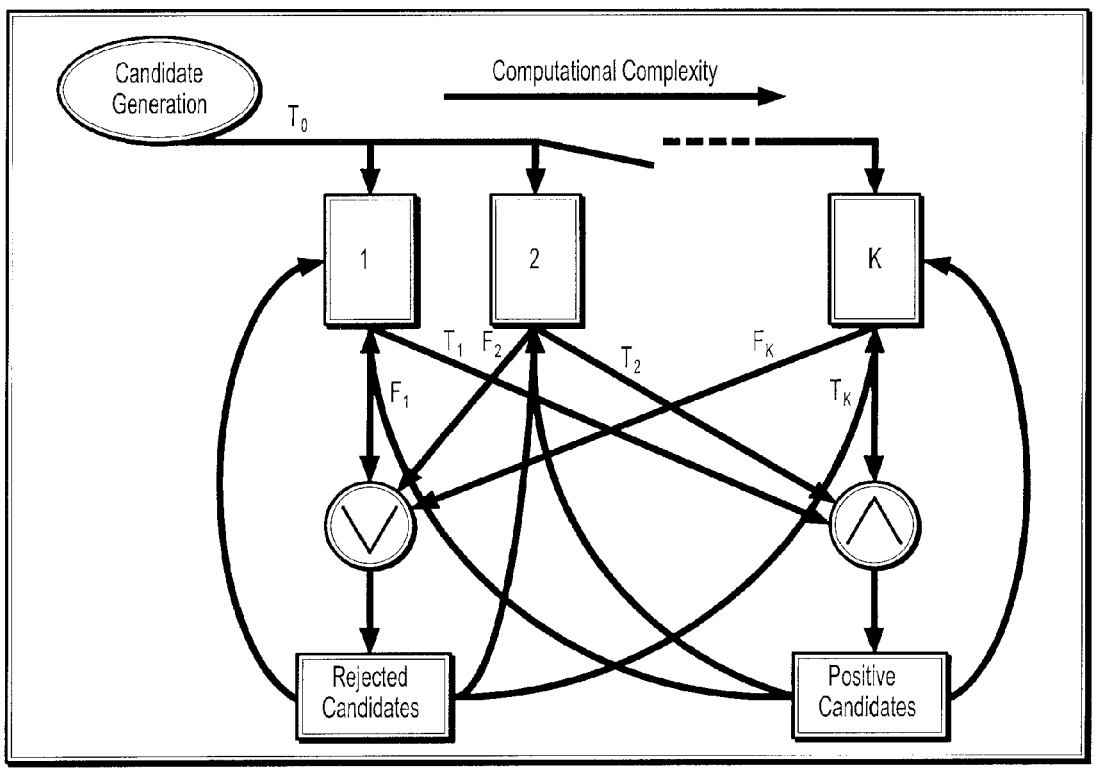
FIG. 2 depicts a cascade framework for offline training of classifiers according to an embodiment of the invention.

An AND-OR cascade framework for offline training of classifiers according to an embodiment of the invention is shown in FIG. 2. The framework of FIG. 2 includes a cascade of classifiers of increasing complexity numbered 1, 2, ..., K. In the framework of FIG. 2, all of the stages in the cascade are trained with the initial training dataset $T_0$, i.e. $\Psi_k = \Psi_0 \forall k$. Candidates rejected at each stage, labeled $F_1, F_2, \ldots, F_K$ are ORed together into a rejected candidates set, indicated by the block labeled v, while the positive candidates from each stage, labeled as $T_1, T_2, \ldots, T_K$, are ANDed together to form the positive candidates set, indicated by the block labeled ^. The arrows leading from the Rejected Candidates block back to the classifier blocks, and the arrows leading from the Positive Candidates block back to the classifier blocks represent the feedback mechanism that exists in the framework between the classifiers. A positive candidate needs to be detected by all the classifiers in the cascade, so if one classifier fails to detect it, then the fact that other classifiers detect does not make a difference. Positive candidate detection is an all or none mechanism. On the other hand, a negative candidate is rejected as long as at least one of the classifiers rejects it. The other classifiers need not correctly classify a negative candidate if it is already correctly classified (i.e., rejected) by one of the other classifiers. To ensure these two conditions there needs to be some implicit connection between the classifiers, represented by these arrows. Note that classifiers trained according to a framework illustrated in FIG. 2 can be used for online classification of object candidates according to the framework illustrated in FIG. 1.

An AND-OR cascade according to an embodiment of the invention optimizes the following cost function:

$$J(\alpha_1, \ldots, \alpha_K) = \sum_{k=1}^{K} \Phi_k(\alpha_k) + v_1 \sum_{i \in C^-} \prod_{k=1}^{K} (e_{ik})_+ + v_2 \sum_{i \in C^+} \max(0, e_{i1}, \ldots, e_{iK}) \quad (3)$$

where $e_{ik} = 1 - \alpha_k^T y_i x_{ik}'$ and $(e_{ik})_+$ defines the hinge loss of the $i^{th}$ training example $\{(x_{ik}', y_i)\}$ induced by classifier k, and $v_1$ and $v_2$ are weighting factors. Notice that classifier k uses a subset of the features in $x_i$, so the feature vector used by classifier k is denoted as $x_{ik}'$. The first term in EQ. (3) is a summation of the regularizers for each of the classifiers in the cascade and the second and third terms account for the losses induced by the negative and positive samples respectively. Unlike the system of EQ. (1), the loss function here is different for positive and negative samples. The loss induced by a positive sample is zero only if $\forall k: 1 - \alpha_k^T y_i x_{ik}' \leq 0$ which corresponds to the "AND" operation in FIG. 2, and the loss induced by a negative sample is zero as long as $\exists k: 1 - \alpha_k^T y x_{ik}' \leq 0$, which corresponds to an "OR" operation.

The objective function in EQ. (3) is nonconvex and nonlinear, which by itself is computationally expensive to solve. In the next section an efficient alternating optimization algorithm is presented to solve this system.

Cyclic Optimization of CCL

An iterative algorithm is developed which, at each iteration, carries out K steps, each aiming to optimize one classifier at a time. This type of algorithms is usually called an alternating or cyclic optimization algorithm. At each iteration, one fixes all of the classifiers in the cascade except the classifier k. The fixed terms have no effect on the optimization of the problem once they are fixed. Hence solving EQ. (3) is equivalent to solving the following system by dropping the fixed terms in EQ. (3):

$$J(\alpha_k) = \Phi_k(\alpha_k) + v_1 \sum_{i \in C^-} w_i (e_{ik})_+ + v_2 \sum_{i \in C^+} \max(0, e_{i1}, \ldots, e_{ik}, \ldots, e_{iK})$$

$$\text{where } w_i = \prod_{m=1, m \neq k}^{K} (e_{im})_+.$$

This can be cast into a constrained system as follows:

$$\min_{(\alpha_k, \xi_i) \in R^{d_k+1}} \Phi_k(\alpha_k) + v_1 \sum_{i \in C^-} w_i \xi_i + v_2 \sum_{i \in C^+} \xi_i, \quad (4)$$

such that $$\xi_i \geq e_{ik}, \forall i,$$
$$\xi_i \geq 0, \forall i \in C^-,$$
$$\xi_i \geq \gamma_i, \forall i \in C^+,$$

where $y_i = \max(0, e_{i1}, \ldots, e_{i(m-1)}, e_{i(m+1)}, \ldots, e_{iK})$.

The subsystem in EQ. (4) is a convex system and differs from the system in EQ. (2) by two changes. First, the weight assigned to the loss induced by the negative samples is now adjusted by the term $$w_i = \prod_{k=1, k \neq m}^{K} (e_{ik})_+.$$

This term multiplies out to zero for negative samples correctly classified by one of the other classifiers. For these samples $e_{im} < 0$ and $\xi_i = 0$ making the constraints on $\xi_i$ in EQ. (4) redundant. As a result there is no need to include these samples when training the stage-m of the cascade, which yields computational advantages. Second, the lower bound for $\xi$ is now $\max(0, e_{i1}, \ldots, e_{i(m-1)}, e_{i(m+1)}, \ldots, e_{iK})$. This implies that if any of the classifiers in the cascade misclassifies $x_{im}$ the lower bound on $\xi$ is no longer zero, relaxing the constraint on $x_{ik}$.

Training AND-OR Cascaded Classifiers

Figure 5:
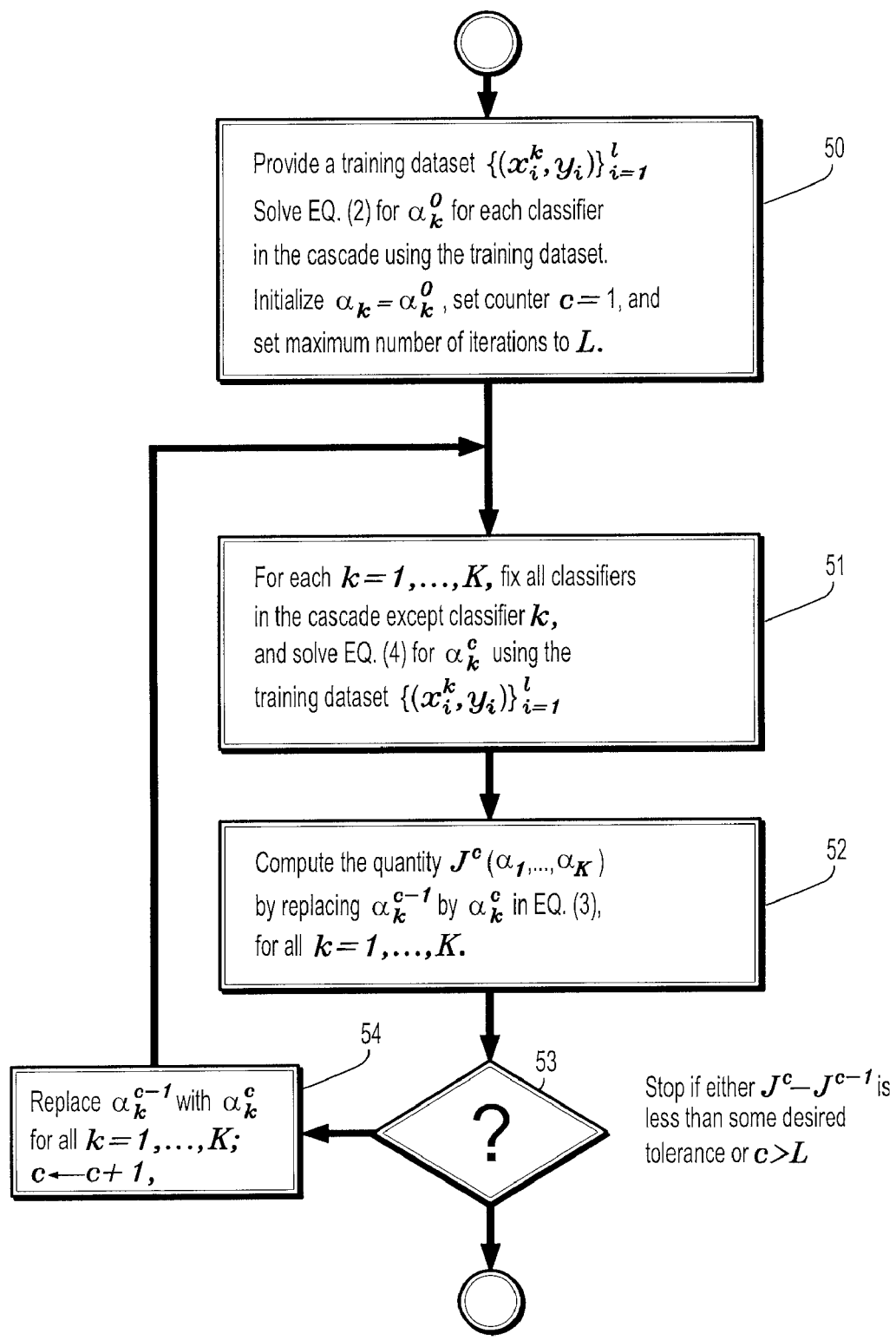
FIG. 5 is a flowchart of a method for offline training of classifiers, according to an embodiment of the invention.

A flowchart of an algorithm according to an embodiment of the invention for AND-OR based training of cascaded class is presented in FIG. 5. Referring now to the figure, at step 50, an algorithm starts by providing a training dataset $\{(x_i^k, y_i)\}_{i=1}^{l}$, and solving EQ. (2) for $\alpha_k^0$ for each classifier in the cascade using the training dataset, then initializing $\alpha_k = \alpha_k^0$, setting a counter $c=1$ and a maximum number of iterations to L. At step 51, all the classifiers in the cascade are fixed except classifier k, and EQ. (4) is solved to calculate a current set of $\alpha_k^c$ using the training dataset $\{(x_i^k, y_i)\}_{i=1}^{l}$. This is repeated for all $k=1, \ldots, K$. At step 52, the quantity $J^c(\alpha_1, \ldots, \alpha_K)$ is computed by replacing $\alpha_k^{c-1}$ by $\alpha_k^c$ in EQ. (3), for all $k=1, \ldots, K$. At step 53, the algorithm stops if either $J^c - J^{c-1}$ is less than some desired tolerance or $c > L$. Otherwise, at step 54, $\alpha_k^{c-1}$ is replaced by $\alpha_k^c$ for all $k=1, \ldots, K$, c is replaced by $c+1$, and the algorithm returns to step 51.

Convergence Analysis

The cyclic optimization algorithm according to an embodiment of the invention presented in FIG. 5 defines a point-to-set algorithmic mapping A which is actually a composite algorithmic mapping since $A = A_1 \circledx \ldots \circledx A_k \circledx \ldots \circledx A_K$. Each sub-mapping $A_k$ is characterized by the system of EQ. (4). In the following, denote $A_k(\hat{\alpha})$ as the algorithmic mapping specified by the system of EQ. (4) where all $\alpha$'s except $\alpha_k$ are fixed to the corresponding values in $\hat{\alpha}$ and $\alpha_k$ is a variable to be determined. In addition, denote $\Delta_k(\hat{\alpha})$ as the feasible region defined through the hinge loss constraints in EQ. (4) in terms of $\hat{\alpha}$ with only $\alpha_k$ free. Note that although omitted, EQ. (4) has other constraints defined by $\alpha_1, \ldots, \alpha_k$, $\alpha_{k+1}, \ldots, \alpha_K$ with fixed values. Hence:

$$A_k(\hat{\alpha}) = \arg\min\{J(\hat{\alpha}_1, \ldots, \hat{\alpha}_{k-1}, \hat{\alpha}_k, \hat{\alpha}_{k+1}, \ldots, \hat{\alpha}_K) | \alpha_k \in \Delta_k(\hat{\alpha})\} \quad (5)$$

where $\hat{\alpha}$ is a given specific value.

The algorithm in FIG. 5 can be re-stated as follows: at the $c^{th}$ iteration, start from the iterate $\alpha=(\alpha_1^c \alpha_2^c \ldots \alpha_K^c)$ and solve:

$$(\alpha_1^{c+1}\alpha_2^c \ldots \alpha_K^c) \in A_1(\alpha^c)$$

$$(\alpha_1^{c+1}\alpha_2^{c+1} \ldots \alpha_K^c) \in A_2(\alpha_1^{c+1}\alpha_1^c \ldots \alpha_K^c)$$

$$\ldots \in \ldots$$

$$(\alpha_1^{c+1}\alpha_2^{c+1} \ldots \alpha_K^{c+1}) \in A_K(\alpha_1^{c+1}\alpha_2^{c+1} \ldots \alpha_K^c)$$

It is challenging to prove the convergence of a cyclic optimization algorithm for local minimizers. For many cyclic approaches, no convergence analysis can be substantially established. It can be proven that an algorithm according to an embodiment of the invention at least converges from any initial point (global convergence) to the set of sub-optimal solutions. The solution $\hat{\alpha}$ is suboptimal if the objective function J can not be further improved at $\hat{\alpha}$ following any directions defined by $\alpha_k$, $k=1, \ldots, K$. In other words, the solution $\hat{\alpha}$ obtained by the algorithm satisfies: $\hat{\alpha}_k$ is a generalized fixed point of $A_k$, i.e., $\hat{\alpha}_k \in A_k(\hat{\alpha})$. The following theorem characterizes the result.

Theorem: (a) The sequence $\{J^c\}$ converges to a finite value $\hat{J}$; (b) for any accumulation point of $\{\alpha^c\}$, denoted as $\hat{\alpha}$, if the operation of minimization over $\Delta_k$ occurs an infinite number of times in the subsequence which has limit $\hat{\alpha}$, then $\hat{\alpha}_k \in A_k(\hat{\alpha})$.

Conclusions (a) and (b) hold if: (1) $\alpha \in \Delta_k(\alpha)$ for all $\alpha$ and k; (2) $\Delta_s$ is upper-semicontinuous and lower-semicontinuous on $\Omega$; (3) if $\beta \in \Delta_k(\alpha)$, then $\Delta_k(\beta) = \Delta_k(\alpha)$; and (4) $\Omega_0 = \{\alpha \in \Omega | J(\alpha) \leq J(\alpha^0)\}$ is compact.

Obviously, $\alpha$ is itself feasible to $\Delta_k(\alpha)$. The only constraint that appears when the unconstrained system EQ. (3) is converted into constrained subsystem EQ. (4) is the hinge loss $\alpha^T y_i x_i + \xi \geq 1$. The function $\alpha^T y_i x_i$ is a continuous function in terms of $\alpha$, so the sets $\{\alpha | \alpha^T y_i x_i < \text{constant}\}$ and $\{\alpha | \alpha | \alpha^T y_i x_i > \text{constant}\}$ are both open sets, proving $\Delta_k$ is upper-semicontinuous and lower-semicontinuous. If a point $\beta \in \Delta_k(\alpha)$, it means $\beta_m = \alpha_m$, for $m=1, \ldots, K$, $m \neq k$. Then $\Delta_k(\beta) = \Delta_k(\alpha)$. The set $\Omega$ is the entire $\alpha$ space. For any initial point $\alpha^0$, let $J^0 = J(\alpha^0)$. Then $J(\alpha) \leq J^0$ implies that $$\sum_{k=1}^K \Phi_k(\alpha_k) \leq \phi$$

which is a constant since the error terms (the second and third terms) in EQ. (3) are nonnegative. The set $$\left\{\alpha \left| \sum_{k=1}^K \Phi_k(\alpha_k) \leq \phi \right.\right\}$$

defines a bounded and closed set, and is thus compact.

CAD Applications

Although an algorithm according to an embodiment of the invention provides a general framework which can be employed for any classification purpose, the approach was motivated by a Computer-Aided Detection (CAD) system which detects abnormal or malignant tissues from medical imaging modality, such as CT, MRI and PET.

Automatic Polyp Detection

Colorectal cancer is the third most common cancer for both men and women. It is estimated that in 2004, nearly 147,000 cases of colon and rectal cancer were diagnosed in the United States, and more than 56,730 people would die from colon cancer, accounting for about 11% of all cancer deaths. In over 90% of the cases, colon cancer progressed rapidly from a local stage (polyp adenomas) to an advanced stage (colorectal cancer), which has very poor survival rates. However, identifying (and removing) lesions (polyps) when still in a local stage of the disease have very high survival rates, thus illustrating the need for early diagnosis.

In the area of colon cancer detection from CT images, the useful aspect of a CAD system is the improvement in sensitivity with respect to polyp detection that such system can offer. In order to put the role of colon CAD as a second reader in proper context, an outline of a complete clinical workflow follows below.

A workflow with integrated Colon CAD system includes the following 4 stages.

(1) Case Loading: a physician loads the case for review, and the CAD system begins processing in the background.
(2) First read: the physician reviews the case, prone and supine, finalizes his/her findings.
(3) CAD results are invoked (CAD button is pressed): the physician acknowledges she/he has completed the review of the case.
(4) Second read: physician reviews additional CAD findings, and rejects any considered false positives.

To avoid any delays in the physician's workflow, the CAD results should be ready by the time physician completes the first read. Therefore there is a run-time requirement a CAD system needs to satisfy. The stages involved during online processing of a volume and the median time it takes are as follows:

(1) Interpolation, 47 sec.;
(2) Detagging, 50 sec.;
(3) Segmentation, 38 sec.;
(4) Candidate Generation, 1 min. 29 sec.;
(5) Feature Computation, 4 min. 46 sec.;
and (6) Classification, negligible.

The total time is 8 min. 14 sec. This timing data, and all timing data presented herein below, were obtained on a computer running an Intel Pentium M 2.10 Ghz CPU.

Feature computation is the most computationally intense stage of the online processing, taking about 57% of the time. This stage can be accelerated by first partitioning the original feature set into subsets with increasing computational costs, then using an AND-OR framework according to an embodiment of the invention to build a cascade classifier in which earlier stages are trained by the less computationally intense features. This way during online execution earlier stages filter out as many candidates as possible before later stages that require advanced features are called upon.

Numerical Results

A cascade classification algorithm according to an embodiment of the invention is validated with respect to its generalization performance and computational efficiency. An algorithm was compared to a single stage SVM classifier constructed using all the features, and to an AdaBoost based cascade classifier.

Data and Experimental Settings

The database of CT images used for validating a classification framework according to an embodiment of the invention were obtained from two different sites across US. The data for 370 patients were randomly partitioned into two groups: a training group with 169 patients, and a test group with 201 patients. The test group data was sequestered and only used to evaluate the performance of the final system.

Training Data Patient and Polyp Info: There were 169 patients with 338 volumes. The candidate generation (CG) algorithm identifies a total of 88 polyps while generating an average of 137.7 false positives (FPs) per volume.

Testing Data Patient and Polyp Info: There were 201 patients with 396 volumes. The candidate generation (CG) algorithm identifies a total of 106 polyps while generating an average of 139.4 false positives per volume.

Candidates were generated from a candidate generation (CG) algorithm that employs a robust blob detection strategy to identify blob-like structures. The output of the CG step is the locations of candidates, along with some internal features that are generated as intermediate results of the candidate generator. These features include simple gray scale statistics and shape based information of the blob. The CG algorithm successfully identifies most of the nodules from the CT scans, including some non-obvious nodule examples. However, the CG also generates a huge number of false positive candidates. After the CG step, a large number of image features are computed for each of the candidates to describe the shape (both 2D and 3D), size, intensity statistics (that describe texture), and template matching. Another set of more advanced and computationally demanding features can be calculated as follows. For each detected candidate region, the target is segmented. A plurality of statistical features, computed in a remapped coordinate system, are derived from the segmented shape of the candidate. The feature set includes local intensity statistics and geometrical features, such as size and anisotropy of the gray values at multiple scales. Furthermore, the intensity homogeneity is represented in a set of entropic measures by using the generalized Jensen-Shannon divergence The candidate generation algorithm was independently applied to the training and test sets, achieving 90.72% detection rate on the training set at 137.7 FPs per volume and 90.91% detection rate on the test set at 139.4 FPs per volume, resulting in a total of 46764 and 55497 candidates in the respective training and test sets.

A total of 46 numerical image features were designed, of which 7 came from the CG step with no extra computational burden. The remaining features were divided into three groups according to their computational costs. A three-stage cascade classifier was built. The first feature set, which was composed of the 17 least computationally intense features, took 0.2 sec. CPU time per candidate, and was used together with the CG features to train the first classifier. The second feature set, which was composed of 7 relatively more computationally intense features, required an average of 0.5 sec. CPU time per candidate, and was used together with feature set 1 and the CG features to train the second classifier. The third feature set, which was composed of the 15 most computationally demanding features, required an average of 1.4 sec. CPU time per candidate, and was used with all the other features to train the third classifier.

Classifier Design

Thirty percent of the training data was set aside as validation data to be used for parameter tuning. During this process, the classifiers are trained with the 70% and are validated with the remaining 30%. However when the tuning process is complete, i.e. the classifier parameters and thresholds are all set, the entire training data is used to train the classifiers. In most CAD applications, 0-5 FPs/vol is defined as the clinically admissible range of false positives per volume. Therefore this region on the ROC curve is set as the region of interest (ROI) and all classifiers are tuned to maximize this portion of the area under the ROC curve with the validation data.

For testing an algorithm according to an embodiment of the invention, the function $\Phi_k(k) = \|\alpha\|_2^2$, which is equivalent to an SVM. The parameters $v_1$ and $v_2$ were estimated from a coarsely tuned discrete set of five values. The values that maximized the area of ROI under the ROC curve for the overall system with the validation dataset are found as $v_1=50$ and $v_2=1$.

In experiments using an AdaBoost cascade, the feature set was split into three groups and a three phase training of the AdaBoost cascade was used. During the first training phase using the first feature set and the CG features, the first $k_1$ stages of the cascade were built. The second feature set was used together with the first feature set and CG features to build the stages $k_1+1$ through $k_1+k_2$ of the cascade in the second training phase. Finally, during the third training phase, all of the features were used and stages $k_2+1$ through $k_2+k_3$ were built. The validation dataset was used to tune the decision thresholds and to estimate the number of stages in each phase, i.e. $k_1$, $k_2$, $k_3$. The decision thresholds at each stage were tuned to satisfy the target sensitivity for each phase. Based on the performance with the validation set, the desired target sensitivities were no polyp miss for phase one and two and one polyp miss per stage for phase three of the training. The number of stages in each phase were estimated to minimize the area of the ROI under the ROC curve. During each phase, the number of stages is increased in a greedy manner until no further increase in this area is observed upon when the next phase starts. Designing the cascade AdaBoost classifier this way yielded one stage for phase 1, one stage for phase 2 and three stages for phase 3, for a five-stage cascade classifier.

An SVM classifier was also designed using all of the features available without any cascading. The parameters $v_1=15$ and $v_2=2$ were estimated using the same approach described above for the proposed AND-OR cascade.

Generalization Performance and Speed

Figures 3, 4:
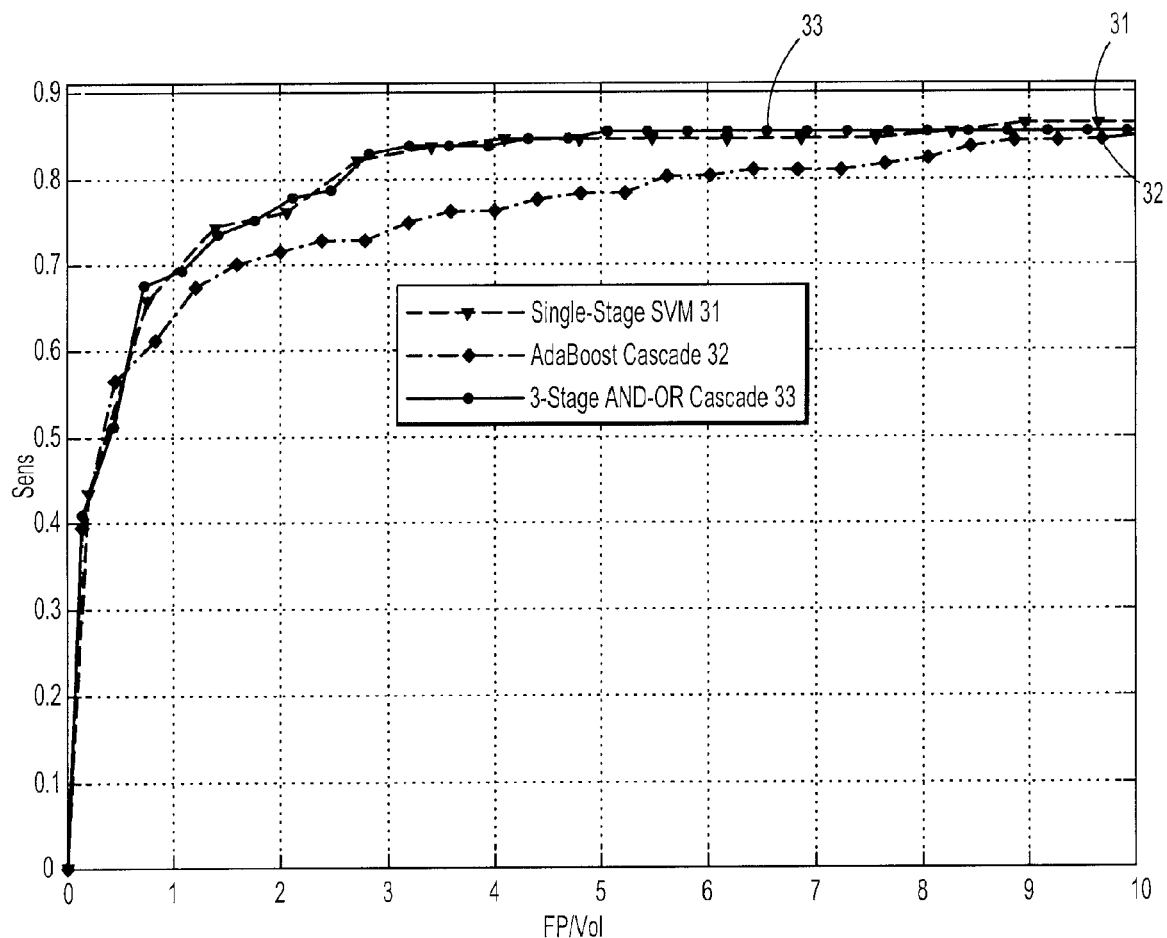
FIG. 3 is a graph of the ROC curves obtained by three classifiers on the test data, according to an embodiment of the invention.
FIG. 4 is a table of results obtained by three different classifiers, according to an embodiment of the invention.

The three classifiers obtained respectively by an AND-OR cascade according to an embodiment of the invention, a single stage SVM, and an AdaBoost cascade were evaluated on the sequestered test set. FIG. 4 is a table of the results, which include the average feature computation time per volume in CPU seconds, the total number of polyps detected and the remaining number of candidates per volume after each stage in the cascade, and the number of false positives per volume, for the three classifiers (and stages were appropriate). Finally, the overall system performance obtained by the three classifiers are compared in FIG. 3 by plotting the ROC curves corresponding to the final stage of the cascade classifiers and the single-stage SVM, in which the sensitivity of each classifier is plotted as a function of the number of false positives. Curve 31 is the single stage SVM ROC curve, curve 32 is the AdaBoost cascade ROC curve, and curve 33 is the ROC curve of an AND-OR cascade according to an embodiment of the invention.

Both cascade classifiers demonstrate computational efficiency compared to single-stage SVM. The AND-OR cascade according to an embodiment of the invention required an average of 81.0 CPU secs. per volume for feature computation across the three stages, the AdaBoost cascade required 118 CPU secs. for feature computation for the three phases (five stages). Both numbers are significantly lower than the 286.0 CPU secs. required for the single-stage SVM. From a performance generalization perspective, there is observed no statistically significant difference between the proposed cascade classifier and the single stage SVM when the ROC curves obtained by these classifiers on the test data are compared. When the AND-OR cascade according to an embodiment of the invention is compared against the AdaBoost Cascade, a roughly 30% improvement is achieved in the average online processing time of a volume and statistically significant improvements are observed in the performance with a p-value-0.002 in favor of the AND-OR cascade. An AND-OR cascade according to an embodiment of the invention improved the online execution time of the CAD system without sacrificing system performance. This is achieved by constructing a series of linear classifiers all trained simultaneously in an AND-OR framework using features of increasing complexity.

To estimate the p-value, one first calculates a critical ratio of two ROC curves, defined as $$z = \frac{|A_1 - A_2|}{\sqrt{E_1^2 + E_2^2 - 2rE_1E_2}},$$

where $A_1$ and $A_2$ are the areas under the two curves, $E_1$ and $E_2$ are the respective standard errors, and r is the estimated correlation between the two areas, and then z is referred to a normal distribution table to determine p.

System Implementation

It is to be understood that embodiments of the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 6:
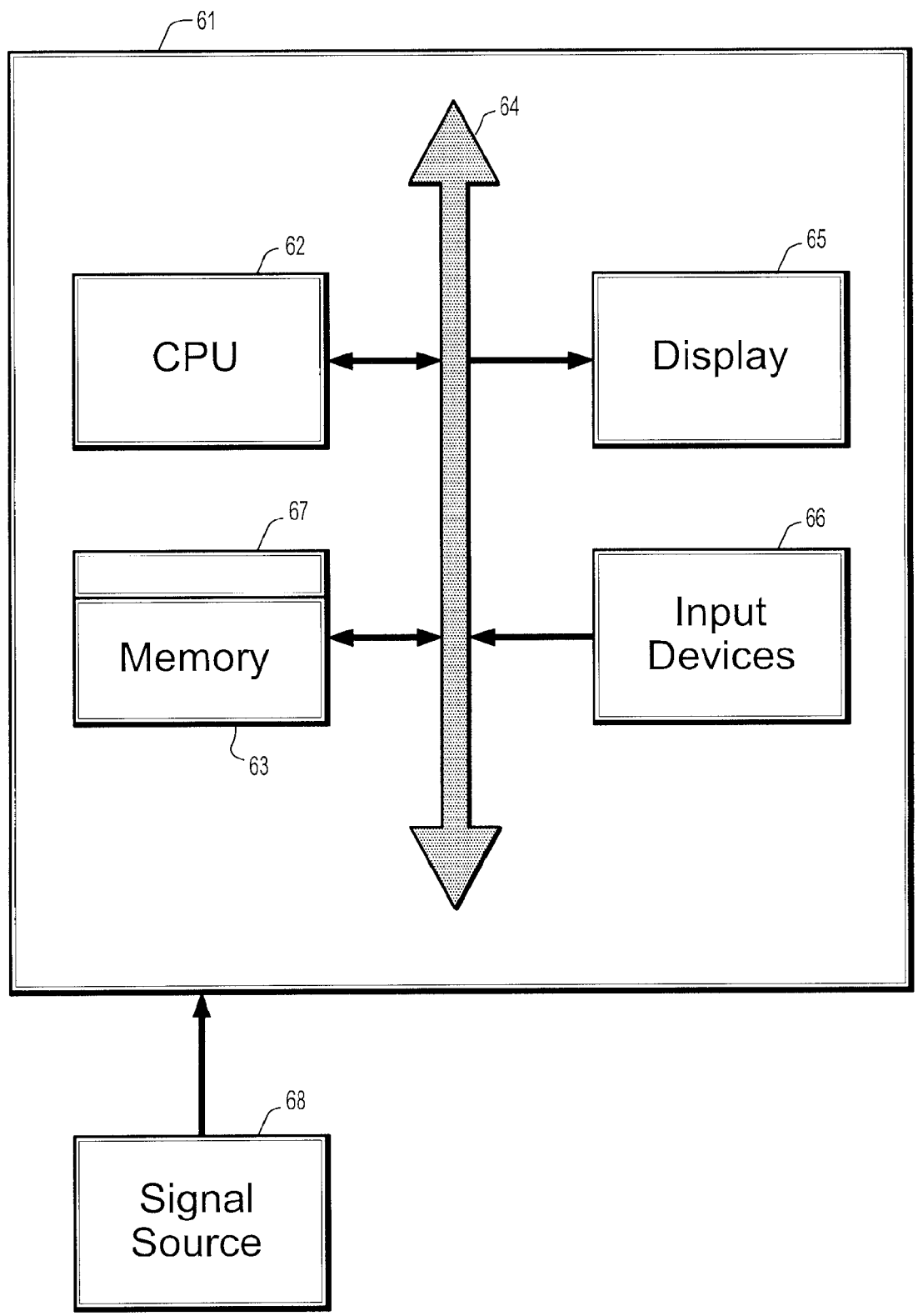
FIG. 6 is a block diagram of an exemplary computer system for implementing a method for offline training of classifiers, according to an embodiment of the invention.

FIG. 6 is a block diagram of an exemplary computer system for implementing a method for offline training of classifiers according to an embodiment of the invention. Referring now to FIG. 6, a computer system 61 for implementing the present invention can comprise, inter alia, a central processing unit (CPU) 62, a memory 63 and an input/output (I/O) interface 64. The computer system 61 is generally coupled through the I/O interface 64 to a display 65 and various input devices 66 such as a mouse and a keyboard. The support circuits can include circuits such as cache, power supplies, clock circuits, and a communication bus. The memory 63 can include random access memory (RAM), read only memory (ROM), disk drive, tape drive, etc., or a combinations thereof. The present invention can be implemented as a routine 67 that is stored in memory 63 and executed by the CPU 62 to process the signal from the signal source 68. As such, the computer system 61 is a general purpose computer system that becomes a specific purpose computer system when executing the routine 67 of the present invention.

The computer system 61 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to a preferred embodiment, those skilled in the art will appreciate that various modifications and substitutions can be made thereto without departing from the spirit and scope of the invention as set forth in the appended claims.

What is claimed is:

1. A computer-implemented method for training classifiers for Computer-Aided Detection in medical images, said method performed by a computer comprising the steps of:

providing an image feature training set $\{(x_i, y_i)\}_{i=1}^{l}$, wherein $x_i \in R^d$ are input feature variables and $y_i \in \{-1,1\}$ are class labels for labeling each variable and a cascade of K classifiers to be trained;

minimizing, for each classifier k, a first cost function $$\Phi(\alpha_k) + \sum_{i=1}^{l} w_i \times \max(0, 1 - \alpha^T y_i x_i^k),$$

to initialize an $\alpha_k^0$ associated with each classifier k, wherein the function $\Phi: R^{(d)} \Rightarrow R$ is a regularization function and $\{w_i: w_i \geq 0, \forall i\}$ is a pre-determined weight associated with $x_i$;

for each classifier k, fixing all classifiers except classifier k and minimizing a second cost function $$\Phi_k(\alpha_k) + v_1 \sum_{i \in C^-} w_i \times \max(0, e_{ik}) + v_2 \sum_{i \in C^+} \max(0, e_{i1}, \ldots, e_{ik}, \ldots, e_{iK})$$

to solve for $\alpha_k^c$ for a counter value c using the training dataset $\{(x_i^k, y_i)\}_{i=1}^{l}$, wherein $$w_i = \prod_{m=1, m \neq k}^{K} \max(0, e_{im}),$$

$e_{ik} = 1 - \alpha_k^T y_i x_{ik}'$ defines a hinge loss of the $i^{th}$ training example $\{(x_{ik}', y_i)\}$ induced by classifier k, $v_1$ and $v_2$ are weighting factors, $C^+$ and $C^-$ are corresponding sets of indices for positive and negative classes respectively, and wherein $x^{ik}$ denotes the subset of features in $x_i$ used by classifier k;

calculating $J^c(\alpha_1^c, \ldots, \alpha_K^c) =$ $$\sum_{k=1}^{K} \Phi_k(\alpha_k^c) + v_1 \sum_{i \in C^-} \prod_{k=1}^{K} \max(0, e_{ik}) + v_2 \sum_{i \in C^+} \max(0, e_{i1}, \ldots, e_{iK})$$

for each classifier k; and comparing $J^c$ with a previous iteration $J^{c-1}$, wherein if $J^c - J^{c-1}$ is less than a predetermined tolerance, said classifier training is completed.

2. The method of claim 1, wherein providing an image feature training set comprises:

providing a set of image features, said features generated from one or more digitized medical images, each said image comprising a plurality of intensities associated with an n-dimensional grid of points;

partitioning said image feature set into a plurality of subsets according to a computational cost of classifying a candidate feature as one of said image features;

developing a feature classifier wherein each image feature subset is associated with a feature classifier; and forming of cascade of said classifiers of increasing complexity.

3. The method of claim 2, further comprising tuning values of said weighting factors $v_1$ and $v_2$ to maximize an area under a receiver operator characteristic (ROC) curve corresponding to a domain of 0 to 5 false positives per image, $$\xi_i \geq 1 - \alpha^T y_i x_i,$$
$$\xi_i \geq 0, \ \forall \ i.$$

4. The method of claim 1, wherein said second cost function is solved as a mathematical programming system $$\min_{(\alpha_k, \xi_k) \in R^{d_k+l}} \Phi_k(\alpha_k) + v_1 \sum_{i \in C^-} w_i \xi_i + v_2 \sum_{i \in C^+} \xi_i,$$

such that $$\xi_i \geq e_{ik}, \ \forall \ i,$$
$$\xi_i \geq 0, \ \forall \ i \in C^-,$$
$$\xi_i \geq \gamma_i, \ \forall \ i \in C^+,$$

wherein $y_i = \max(0, e_{i1}, \ldots, e_{i(m-1)}, e_{i(m+1)}, \ldots, e_{iK})$.

5. The method of claim 1, wherein said first cost function is solved as a mathematical programming system $$\min_{(\alpha, \xi) \in R^{d+1}} \Phi(\alpha) + \sum_{i=1}^{l} w_i \xi_i$$

such that $$\xi_i \geq 1 - \alpha^T y_i x_i,$$
$$\xi_i \geq 0, \ \forall \ i.$$

6. The method of claim 1, wherein said trained classifiers are adapted to being used in a cascade of classifiers of increasing complexity that detect and classify regions of interest in incoming medical images.

7. The method of claim 1, wherein $\Phi(\alpha) = \|\alpha\|_2^2$.

8. The method of claim 1, wherein $\Phi(\alpha) = |\alpha|$.

9. The method of claim 1, further comprising incrementing a counter c, and terminating said training if said counter becomes greater than a pre-determined maximum.

10. A computer-implemented method for training classifiers for Computer-Aided Detection in medical images, said method performed by a computer comprising the steps of:

providing an image feature training set $\{(x_i, y_i)\}_{i=1}^{l}$, wherein $x_i \in R^d$ are input feature variables and $y_i \in \{-1,1\}$ are class labels for labeling each variable and a cascade of K hyperplane classifiers to be trained;

training said cascade of hyperplane classifiers using said training set wherein a negative candidate is correctly classified by said cascade when it is rejected by at least one of said classifiers, and a positive candidate is correctly classified if it is detected by all of the classifiers in the cascade;

wherein training said cascade of hyperplane classifiers comprises providing an initial set $\alpha_k^0$ associated with each classifier k by minimizing, for each classifier k, a first cost function $$\Phi(\alpha_k) + \sum_{i=1}^{l} w_i \times \max(0, 1 - \alpha^T y_i x_i^k)$$

wherein the function $\Phi: R^{(d)} \Rightarrow R$ is a regularization function and $\{w_i: w_i \geq 0, \forall i\}$ is a pre-determined weight associated with $x_i$;

and, at each iteration of the classifier training, given a set $\alpha_k^c$ from a previous iteration, solving for $\alpha_k^{c+1}$ for each classifier k by fixing all classifiers except classifier k and minimizing a second cost function $$\Phi_k(\alpha_k) + v_1 \sum_{i \in C^-} w_i \times \max(0, e_{ik}) + v_2 \sum_{i \in C^+} \max(0, e_{i1}, \ldots, e_{ik}, \ldots, e_{iK})$$

using the training dataset $\{(x_i^k, y_i)\}_{i=1}^{l}$, wherein $$w_i = \prod_{m=1, m \neq k}^{K} \max(0, e_{im}),$$

$e_{ik} = 1 - \alpha_k^T y_i x'_{ik}$ defines a hinge loss of the $i^{th}$ training example $\{(x_{ik}', y_i)\}$ induced by classifier k, $v_1$ and $v_2$ are weighting factors, $C^+$ and $C^-$ are corresponding sets of indices for positive and negative classes respectively, and $x_{ik}'$ denotes the subset of features in $x_i$ used by classifier k.

11. The method of claim 10, further comprising calculating a third cost function $$J^{c+}(\alpha_1^{c+1}, \ldots, \alpha_K^{c+1}) = \sum_{k=1}^{K} \Phi_k(\alpha_k^{c+1}) + v_1 \sum_{i \in C^-} \prod_{k=1}^{K} \max(0, e_{ik}) + v_2 \sum_{i \in C^+} \max(0, e_{i1}, \ldots, e_{iK})$$

from the set of $\alpha_k^{c+1}$ for each classifier k; and comparing $J_{c+1}$ with a previous iteration $J^c$ to determine if said training is complete.

12. A program storage device readable by a computer, tangibly embodying a program of instructions executable by the computer to perform the method steps for training classifiers for Computer-Aided Detection in medical images, said method comprising the steps of:

providing an image feature training set $\{(x_i, y_i)\}_{i=1}^{l}$, wherein $x_i \in R^d$ are input feature variables and $y_i \in \{-1,1\}$ are class labels for labeling each variable and a cascade of K classifiers to be trained;

minimizing, for each classifier k, a first cost function $$\Phi_k(\alpha_k) + \sum_{i=1}^{l} w_i \times \max(0, 1 - \alpha^T y_i x_i^k)$$

to initialize an $\alpha_k^0$ associated with each classifier k, wherein the function $\Phi: R^{(d)} \to R$ is a regularization function and $\{w_i: w_i \geq 0, \forall i\}$ is a pre-determined weight associated with $x_i$;

for each classifier k, fixing all classifiers except classifier k and minimizing a second cost function $$\Phi_k(\alpha_k) + v_1 \sum_{i \in C^-} w_i \times \max(0, e_{ik}) + v_2 \sum_{i \in C^+} \max(0, e_{i1}, \ldots, e_{ik}, \ldots, e_{iK})$$

to solve for $\alpha_k^c$ for a counter value c using the training dataset $\{(x_i^k, y_i)\}_{i=1}^{l}$, wherein $$w_i = \prod_{m=1, m \neq k}^{K} \max(0, e_{im}), e_{ik} = 1 - \alpha_k^T y_i x'_{ik}$$

defines a hinge loss of the $i^{th}$ training example $\{(x_{ik}', y_i)\}$ induced by classifier k, $v_1$ and $v_2$ are weighting factors, $C^+$ and $C^-$ are corresponding sets of indices for positive and negative classes respectively, and wherein $x_{ik}'$ denotes the subset of features in $x_i$ used by classifier k;

calculating $$J^c(\alpha_1^c, \ldots, \alpha_K^c) =$$

$$\sum_{k=1}^{K} \Phi_k(\alpha_k^c) + v_1 \sum_{i \in C^-} \prod_{k=1}^{K} \max(0, e_{ik}) + v_2 \sum_{i \in C^+} \max(0, e_{i1}, \ldots, e_{iK})$$

for each classifier k; and
comparing $J^c$ with a previous iteration $J_{c-1}$, wherein if $J^c - J^{c-1}$ is less than a predetermined tolerance, said classifier training is completed.

13. The computer readable program storage device of claim 12, wherein providing an image feature training set comprises:
providing a set of image features, said features generated from one or more digitized medical images, each said image comprising a plurality of intensities associated with an n-dimensional grid of points;
partitioning said image feature set into a plurality of subsets according to a computational cost of classifying a candidate feature as one of said image features;
developing a feature classifier wherein each image feature subset is associated with a feature classifier; and
forming of cascade of said classifiers of increasing complexity.

14. The computer readable program storage device of claim 13, the method further comprising tuning values of said weighting factors $v_1$ and $v_2$ to maximize an area under a receiver operator characteristic (ROC) curve corresponding to a domain of 0 to 5 false positives per image.

15. The computer readable program storage device of claim 12, wherein said second cost function is solved as a mathematical programming system $$\min_{(\alpha_k, \xi_k) \in R^{d_k+1}} \Phi_k(\alpha_k) + v_1 \sum_{i \in C^-} w_i \xi_i + v_2 \sum_{i \in C^+} \xi_i,$$

such that $$\xi_i \geq e_{ik}, \forall i,$$
$$\xi_i \geq 0, \forall i \in C^-,$$
$$\xi_i \geq \gamma_i, \forall i \in C^+,$$

wherein $y_i = \max(0, e_{i1}, \ldots, e_{i(m-1)}, e_{i(m+1)}, \ldots, e_{iK})$.

16. The computer readable program storage device of claim 12, wherein said first cost function is solved as a mathematical programming system $$\min_{(\alpha, \xi) \in R^{d+1}} \Phi(\alpha) + \sum_{i=1}^{l} w_i \xi_i$$

such that $$\xi_i \geq 1 - \alpha^T y_i x_i,$$
$$\xi_i \geq 0, \forall i.$$

17. The computer readable program storage device of claim 12, wherein said trained classifiers are adapted to being used in a cascade of classifiers of increasing complexity that detect and classify regions of interest in incoming medical images.

18. The computer readable program storage device of claim 12, wherein $\Phi(\alpha) = \|\alpha\|_2^2$.

19. The computer readable program storage device of claim 12, wherein $\Phi(\alpha) = |\alpha|$.

20. The computer readable program storage device of claim 12, the method further comprising incrementing a counter c, and terminating said training if said counter becomes greater than a pre-determined maximum.

* * * * *